United States Patent [19]

Roberts

[11] Patent Number: 5,393,791
[45] Date of Patent: * Feb. 28, 1995

[54] HOMOGENEOUS, ESSENTIALLY NONAQUEOUS ADJUVANT COMPOSITIONS WITH BUFFERING CAPABILITY

[75] Inventor: Johnnie R. Roberts, Memphis, Tenn.

[73] Assignee: Helena Chemical Company, Memphis, Tenn.

[*] Notice: The portion of the term of this patent subsequent to Jan. 12, 2010 has been disclaimed.

[21] Appl. No.: 960,894

[22] Filed: Oct. 14, 1992

Related U.S. Application Data

[63] Continuation-in-part of Ser. No. 554,359, Jul. 19, 1990, Pat. No. 5,178,795.

[51] Int. Cl.$^6$ .................... A01N 27/00; B01F 17/44; B01F 17/54; B01J 13/00
[52] U.S. Cl. ................. 514/762; 71/DIG. 1; 252/312; 252/351; 252/DIG. 1; 514/941
[58] Field of Search ............... 252/312, 356, DIG. 1; 514/941, 762; 71/DIG. 1

[56] References Cited

U.S. PATENT DOCUMENTS

| | | | |
|---|---|---|---|
| 2,380,166 | 7/1945 | Griffin | 252/312 X |
| 3,071,550 | 1/1963 | Altscher et al. | 71/DIG. 1 |
| 3,894,149 | 7/1975 | Mast | 71/DIG. 1 |
| 3,898,075 | 8/1975 | Freund et al. | 71/DIG. 1 |
| 3,997,322 | 12/1976 | Ratledge | 71/93 |
| 4,097,403 | 6/1978 | Tsutsumi et al. | 252/DIG. 1 |
| 4,224,049 | 9/1980 | Devisetty et al. | 71/DIG. 1 |
| 4,313,847 | 2/1982 | Chasin et al. | 252/356 |
| 4,637,830 | 1/1987 | Dyer et al. | 71/DIG. 1 |
| 4,755,207 | 7/1988 | Bannon | 71/DIG. 1 |
| 4,834,908 | 5/1989 | Hazen et al. | 252/356 |
| 4,851,421 | 7/1989 | Iwasaki et al. | 514/941 X |
| 4,944,949 | 7/1990 | Story et al. | 514/914 X |
| 4,966,728 | 10/1990 | Hazen | 252/356 X |
| 5,178,795 | 1/1993 | Roberts | 252/356 |
| 5,206,021 | 4/1993 | Dookhith et al. | 514/938 X |

FOREIGN PATENT DOCUMENTS

703607  2/1965  Canada ............ 71/DIG. 1

OTHER PUBLICATIONS

Rose et al.: *The Condensed Chemical Dictionary*, Sixth Edition, Reinhold Publishing Corp., New York (1961), p. 858.

Simanton et al.: "Recommended Specifications for Citrus Spray Oils in Florida", Reprint from vol. 79 of Proceedings of the Florida State Horticultural Society, Miami, Oct. 24–27, 1966, pp. 26–30.

*Primary Examiner*—Richard D. Lovering
*Attorney, Agent, or Firm*—Connolly & Hutz

[57] ABSTRACT

A homogenous, essentially nonaqueous adjuvant composition comprising a spray oil and a surfactant blend selected from the group consisting of sorbitan fatty acid ester, polyethoxylated derivative of a sorbitan fatty acid ester, fatty alkanolamides, peg esters, silicone surfactants, ethoxylated fatty acids, alkyl ethoxylates, alkylphenol ethoxylates, polypropylene glycols, and amine ethoxylates and a buffering agent selected from the group consisting of alkylaryl polyethoxy phosphate ester, $C_1$–$C_6$ carboxylic acids, $C_1$–$C_6$ dicarboxylic acids, phosphoric acid, citric acid, glutaric acid, gluconic acid, lactic acid, glycolic acid, acrylic acid, carboxylated alcohol ethoxylate

R—O $(CH_2CH_2O)_X$H

R=C–$C_{25}$ carboxylic acid, and

X=1–20 moles ethylene oxide in an amount sufficient to reduce the pH to below 7.

20 Claims, No Drawings

HOMOGENEOUS, ESSENTIALLY NONAQUEOUS ADJUVANT COMPOSITIONS WITH BUFFERING CAPABILITY

CROSS REFERENCE TO RELATED APPLICATION

This application is a continuation-in-part of Ser. No. 07/554,359, which was filed Jul. 19, 1990, and is issued U.S. Pat. No. 5,178,795.

The present invention relates to the field of agricultural, forestry, turf, ornamental, industrial, aquatic, rights-of-ways and other applications where pesticides are used and, more specifically, to adjuvant compositions which improve the chemical and physical properties of a pesticide such as an herbicide, insecticide or fungicide.

BACKGROUND OF THE INVENTION

In order to enhance or modify the chemical and/or physical characteristics of certain pesticides, certain materials are added to form a mixture for spraying. Generally referred to as adjuvants, these materials have no pesticidal activity of their own. Since spray application can be critical to the performance of the agricultural chemical, adjuvants are added to reduce application problems such as chemical stability, incompatibility, solubility, suspension, foaming, drift, evaporation, volatilization, phytotoxicity, surface tension, droplet size and coverage. They can, depending on their type, enhance wetting, spreading, sticking, emulsifying, dispersing and biological activity. Adjuvants include wetting agents, crop oil concentrates, spreaders, stickers, buffering agents, foaming and anti-foaming agents, dispersing agents and drift control agents. Over 200 EPA-registered pesticides have specific recommendations on their labels for adjuvant use. These are recommended for one of two reasons—or both. First, to enhance biological activity of the pesticide and second, to reduce, minimize or eliminate spray application problems as noted previously. There are several different types of adjuvants recommended. To achieve consistent, effective results from them, the user must first select the desired type of adjuvant and then the appropriate product within that specific type for use with a particular pesticide and then use that product at recommended rates.

It is known that petroleum hydrocarbon spray oils increase the efficacy of herbicides, fungicides and other pesticides by enhancing the deposition characteristics and wetting and spreading of the spray solution resulting in a more even and uniform spray deposit or by increasing the biological effect of certain pesticides. Such spray oils can increase penetration and slow evaporation. Paraffin based spray oil is a petroleum oil used as dormant spray, summer oil, carrier for pesticides or an adjuvant to increase the efficacy of agricultural chemicals.

In U.S. Pat. No. 3,977,322, an agricultural spray oil composition comprising a major amount of a petroleum oil and a minor amount of a vegetable oil is disclosed as providing a particularly improved carrier which enhances the effectiveness of selective herbicides. These compositions also include ionic and nonionic surfactants such as fatty acid amides of alkanol amines and alkyl substituted phosphoric acids.

A synergistic herbicidal composition is disclosed in U.S. Pat. No. 4,755,207 and comprises a non-phytotoxic crop oil, a surfactant, and hydrophobic mycoherbicide spore. The oils are once refined vegetable oils or highly refined paraffinic material. The surfactant can be anionic, cationic or nonionic.

Some applications require the separate addition of buffering agents to adjust the pH of alkaline waters used to make up the spray solutions. The buffering agents regulate solution pH to avoid hydrolysis of pesticides that tend to decompose in alkaline spray solutions. Generally, the spray's Ph should be adjusted to a range of 4 to 6 or slightly acidic. Known buffering agents include alkyl aryl polyethoxy ethanol phosphates and organic phosphatic acids as the principal functioning agents. Typically, such a buffering agent is added to the water which is then combined with the pesticide and any other adjuvants required.

U.S. Pat. No. 4,244,049 relates to aqueous-lower alkanol solutions containing alkylaryl polyoxyethylene glycol phosphate esters which act as compatibility agents for mixtures of liquid fertilizer and pesticides. The solution contains about 20% methanol, about 16% water and about 64% of the phosphate ester.

A biocidal fine powder and an agricultural suspension containing the fine powder and an adjuvant are disclosed in U.S. Pat. No. 4,851,421. The adjuvant can be a polyoxyalkylene-type nonionic surface active agent or polyoxyalkylene alkyl or alkylaryl ether phosphates or their salts. The composition does not include any oil components.

It is advantageous to reduce the separate addition of each of the adjuvants to the herbicide or pesticide to save time and to reduce possibility of error in the amounts added since mixing is typically done in the field by unskilled workers. However, the components of an adjuvant composition must form a homogeneous liquid mixture, not a slurry or suspension. Otherwise, the amount of oil and surfactant in the spray will vary form use to use and these variations would adversely affect the physical properties of the spray. In the prior compositions, adjuvants such as buffering agents have been added to the water, then combined with the other adjuvants and the active ingredient because the phosphate compounds used as buffering agents are hydrophilic polar compounds. It is difficult to combine such compounds with oil and obtain a homogeneous composition having the desired spray uniformity and coverage.

It is the object of this invention to provide an essentially non-aqueous, single-phase adjuvant composition containing oil plus surfactant blend and which provides buffering capability. Even after the addition of alkaline water and pesticides, use of this composition reduces and/or maintains the pH of the spray mixture within a desired range to prevent hydrolysis of the pesticide.

SUMMARY OF THE INVENTION

The present invention is a homogeneous, essentially nonaqueous adjuvant composition comprising a spray oil, a blend of surfactants and a buffering agent. When mixed with a pesticide, the composition provides one-step addition of the adjuvants to obtain a more uniform spread of the spray solution of the herbicide or pesticide, improved penetration and slower evaporation. The presence of the buffering agent maintains the pH of the mixture within a desired range pH below 7 in the presence of alkaline waters typically used in spray solutions.

DETAILED DESCRIPTION OF THE INVENTION

This invention is a homogeneous, essentially nonaqueous adjuvant composition having buffering capability. According to the process of this invention, the adjuvant composition comprises a spray oil and a blend of surfactants and buffering agent.

The spray oils utilized in this composition should range from 85% unsolfonated residue UR) to 100. The oil in combination with one or more of the buffering agents above should be mixed with one or more of the surfactants below: in the range of 5.0 to 19.5% by weight. The preferred blend of surfactants include but are not limited to sorbitan fatty acid ester, polyethoxylated derivative of a sorbitan fatty acid ester, fatty alkanolamides of the formula

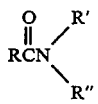

wherein R is $C_6$-$C_{25}$ alkyl group; R and R'' are independently selected from the group consisting of hydrogen, —$CH_2CH_2OH$ or

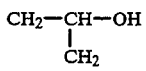

peg esters of the formula

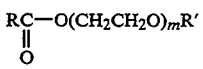

wherein R=$C_2$-$C_{25}$ fatty alkyl, R'=$C_2$-$C_{25}$ fatty alkyl or -H and m=1 to 100, silicone surfactants of the formula

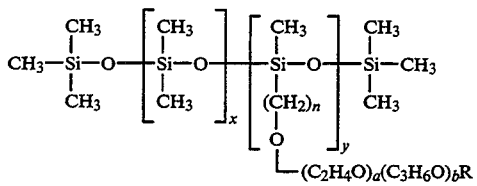

wherein R, R'=$C_1$-$C_{20}$ alkyl, x=0 to 5, a=3 to 25, b=0 to 25, n=2 to 4 and R=—H (or an alkyl group having 1 to 4 carbon atoms (or an alkyl ester group having 1 to 4 carbon atoms, ethoxylated fatty acids

wherein R=$C_6$-$C_{25}$ alkyl group, n=1 to 100, alkyl ethoxylates

wherein R=alkyl group and x=1 to 100, alkylphenol ethoxylates

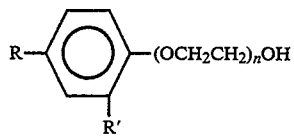

wherein R=H or $C_1$-$C_{20}$ alkyl, R'=H or $C_1$-$C_{20}$ alkyl and n=1 to 100, polypropylene glycols

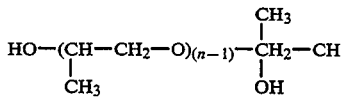

wherein n=1 to 100, or amine ethoxylates

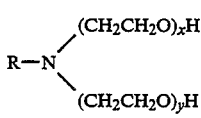

wherein x, y=1 to 100 and R=$C_1$-$C_{25}$ alkyl.

The preferred buffering agent are used at 0.5 to 10% by weight in the formulation. The amount will be determined by the ability of the composition to reduce pH values of the pesticide spray mix to 7 or less. The most preferred would be one in which the pH reduction could be accomplished by using no more than 0.5% by volume of the final composition.

The preferred buffering agents include but are not limited to alkylaryl polyethoxy phosphate ester, $C_1$-$C_6$ carboxylic acids, $C_1$-$C_6$ dicarboxylic acids, phosphoric acid, citric acid, glutaric acid, gluconic acid, lactic acid, glycolic acid, acrylic acid, and carboxylated alcohol and ethoxylate.

The spray oil used in the compositions of this invention is an agricultural spray oil which is a petroleum hydrocarbon oil. These spray oils are the refined fraction of petroleum oil and the preferred petroleum oil is a paraffin oil which is a blend of $C_{10}$- $C_{18}$ saturated aliphatic hydrocarbons. Spray oils are characterized by specifications such as unsulfonated residue, API-gravity, distillation range and pour point. A high unsulfonated residue (UR) indicates a minimum of reactive material in the spray oil and the oil's degree of refinement. This UR value corresponds to about 100% minus the aromatic content. Kerosine, coal oil, naphtha and diesel fuel are all phytotoxic and exhibit low UR values due to their reactivity. Paraffinic oils that have high UR values exhibit little or no phytotoxicity. A minimum of 92% UR is typically required for agricultural spray oils. A spray oil with a 31 -34 API gravity indicates a high degree of paraffinic oil content. An API gravity value of 23 or less indicates an oil with aromatic and napthenic constituents. As a result, such oils are more reactive and phytotoxic. The distillation range determines physical properties of spray oils. Also, a high boiling range is an indication of an oil's phytotoxicity. Lower boiling ranges indicate that the oil has an increased evaporation rate and lower tenacity.

Agricultural spray oils useful in the compositions of this invention have distillation ranges between about 400 to about 500° F. Pour point values reflect the wax content of spray oils. A high value indicates a large amount of wax in the oil. Waxes reduce the spreading and penetration properties of the spray oil. The spray oils used in the present invention have pour points no greater than about 20° F. Generally, oils having a distillation range of 400°–435° F. are used in adjuvants for fungicide and pesticide applications. Oils having a distillation range of 445°–500° F. are employed in adjuvants applications directed at herbicides. As noted previously, the higher boiling oils have increased phytotoxicity which is useful when the objective is to enhance the effectiveness of some contact-type herbicides.

The following table illustrates typical specifications of spray oils useful in the compositions of this invention.

| Gravity API | 32.8 | 34.3 | 34.6 | 33.0 |
|---|---|---|---|---|
| Density | 0.8608 | 0.8530 | 0.8515 | 0.8597 |
| Unsulfonated Residue % | 99.0 | 99.0 | 99.0 | 93–97 |
| Pour Point °F. Max | −5 | −5 | −5 | −5 |
| Distillation D1160 °F. at 10 MM HG | | | | |
| 50% Recovered | 404 | 435 | 454 | 465–471 |
| Range 10–90% | 55 | 72 | 80 | |
| Viscosity CST C40° C. | 10.7 | 13.59 | 14.8 | 21.4 |
| SUS 100° F. | 60 | 70 | 82 | 112 |
| Flash °F. | 335 | 345 | 376 | 385 |
| Color | LO.5 | LO.5 | LO.5 | LO.5 |
| Pounds Per Gal. | 7.171 | 7.106 | 7.119 | 7.162 |

The blend of nonionic surfactants is a blend of acidified sorbitan fatty acid esters, polyethoxylated derivatives of sorbitan fatty acid esters and alkylaryl polyethoxylated phosphate esters. The sorbitan fatty acid ester is acidified by addition of 2.5% by weight of the total blend of a 50% by weight solution of a weak organic acid such as citric acid. Other weak organic acids such as acetic and propionic acid could be used. Additional acidification and solubility enhancement can be obtained by the addition of about 3% by weight oleic acid to the acidified ester. The sorbitan fatty acid esters useful in this invention have the following general

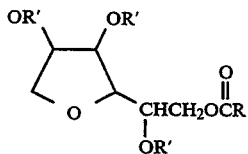

where R is $C_6$–$C_{20}$, R' is hydrogen or —C—R Useful esters include sorbitan monolaurate, sorbitan monopalmitate, sorbitan monooleate, sorbitan monostearate, sorbitan trioleate, and sorbitan tristearate. Sorbitan trioleate is the preferred ester.

The polyethoxylated sorbitan ester component of the blend contains 20 moles of ethylene oxide and has a final HLB of 11.0. This component makes up about 75% by weight of the total blend. Polyethoxylated sorbitan esters which can be used in the blend have the following general formula:

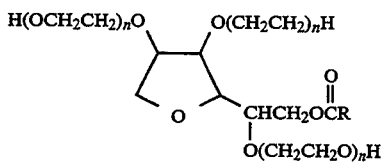

where $R_1$ is $C_6$–$C_{20}$ and n is 1 to 20. Suitable ethoxylated esters include those derived from sorbitan monolaurate (20 moles ethylene oxide), sorbitan monolaurate (4 EO), sorbitan monopalmitate (20 EO), sorbitan monostearate (20 EO), sorbitan monostearate (4 EO), sorbitan tristearate (20 EO), sorbitan monooleate (20 EO), sorbitan monooleate (5 EO) and sorbitan trioleate (20 EO).

The alkylaryl polyethoxylated phosphate esters useful in the compositions of the present invention are esters having the following formula:

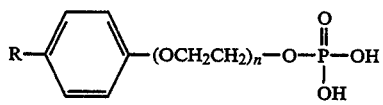

in which R is an alkyl group of 6 to 12, preferably 9 carbon atoms, n is 4 to 6. These esters are known, commercially available surfactants. The preferred ester is a nonyl phenol ethoxylate ester of phosphoric acid wherein n is 4.

Other ingredients which can be added to the homogeneous composition include propylene glycol, dipropylene glycol and petroleum distillates. Such additives are added only if needed and the amount added of each is 5% by weight or less. The compositions of the present invention are essentially nonaqueous which means that the amount of water in the compositions of this invention does not exceed 10% by weight of the total composition, preferably 8% by weight, most preferably 3% by weight. However, some water is typically present due to the presence of water in the surfactants.

Adjuvant compositions according to the present invention are prepared by acidifying the sorbitan fatty acid ester with a weak organic acid such as citric acid. The acidified ester is then mixed with the polyethoxylated sorbitan fatty acid ester to provide an emulsifier blend. The blend is added to the appropriate petroleum hydrocarbon oil. The buffering agent is added to the oil/emulsifier mixture with additional agitation to provide a clear solution. If necessary, water can be added in small increments, e.g., 0.25% by weight, but the amount added is kept to a minimum.

The adjuvant composition of this invention is useful with a broad range of pesticides where an oil concentration adjuvant is recommended. If applied properly, these adjuvant compositions can be used with fertilizer products and herbicides. Optimum applications and effects can be influenced by the crop, pest, spray equipment, spray volume, pressure, droplet size, spray mixture, environmental factors and other factors, Consequently, observation of the spray deposit is typically made and the adjuvant concentrations are adjusted accordingly. In mixing the adjuvant compositions with the pesticide or herbicide, the spray tank is filled one-half full with water and agitated. The pesticide and/or fertilizer is added as directed by labeling or in the following sequence: dry flowables or water dispersible granules, wettable powders, flowables, solutions and emulsifiable concentrates. The filling of the tank with water is continued and the adjuvant composition is added last and agitation is continued.

The pesticide or herbicide compositions containing the adjuvant compositions of the present invention can be applied by ground, aerial or aquatic spray equipment. In most cases, enough of the composition is applied to allow for adjustment of the spray pH to the desired range and uniform wetting and deposition of the spray on the leaf surfaces without undue runoff. For ground application, 1–4 pints are used in 20–100 gallons of spray solution per acre. Concentration should not exceed 1.5% v/v. For low volume aerial application, 2–8 fl. oz. per acre are typically used. In an aquatic application, 1–4 pints per acre are used not to exceed 1.5% v/v concentration.

EXAMPLES

Example 1

A mixture of 94.5 parts sorbitan trioleate and 3 parts oleic acid was heated to 60° F. and stirred continuously until the mixture was homogeneous. Two and one half parts of a 50% citric acid solution in water were added to the mixture sufficient agitation to obtain solution and/or dispersion of the aqueous acid. The final mixture provided an acidified sorbitan fatty acid ester. The mixture was then mixed at a 1:3 weight ratio with a polyethoxylated sorbitan trioleate containing 20 moles of ethylene oxide. The final emulsifier blend consisted of 75% by weight polyethoxylated sorbitan trioleate and 25% by weight acidified fatty acid ester. The blend was then added (18% by weight) to a paraffinic oil, SUN SPRAY 11NTM (supplied by Sun Oil Company), a 100 viscosity spray oil with a distillation range of 465°–471° C. The emulsifier blend and oil were agitated for 15 minutes utilizing a low speed prop type mixture. Two percent by weight of a phosphorylated nonyl phenol ethoxylate containing 5 moles of ethylene oxide was added to the emulsifier/oil mixture and the resulting composition was agitated for an additional 15 minutes. At the end of the blending period, the resulting composition was clear and free of turbidity. The resulting composition (Composition 1) had the following components:

| *COMPONENT | % | FUNCTION |
| --- | --- | --- |
| PARAFFIN OIL | 80.0 | PESTICIDE ACTIVITY ENHANCEMENT |
| POE SORBITAN TRIOLEATE | 12.0 | EMULSIFIER FOR OIL-SURFACTANT FOR S.T. REDUCTION |
| SORBITAN TRIOLEATE | 2.0 | EMULSIFIER FOR OIL |
| OLEIC ACID | 2.0 | ACIDIFIER AND SOLUBILITY AID |
| POE ALKYL ARYL PHOSPHATE | 2.0 | ACIDIFIER AND BUFFERING AGENT |
| PROPYLENE GLYCOL | 1.5 | COUPLING AGENT FOR EMULSIFIER/OIL |
| CITRIC ACID (50) | .5 | ACIDIFIER |
| | 100.0 | |

*COMPOSITION MAY VARY DUE TO RAW MATERIALS

Comparative example A

A composition (Composition A) having the composition shown below is prepared to show the need to use the sorbitan ester and the phosphate ester to obtain the advantages produced by the adjuvant compositions of the present invention.

| Ingredient | % |
| --- | --- |
| Paraffin Oil | 83.0 |
| 4 POE Sorbitan trioleate | 12.0 |
| Sorbitan trioleate | 1.5 |
| Propylene glycol | 2.0 |
| Water | 1.5 |
| | 100.0 |

The following comparison shows that when the phosphate ester is omitted, the performance of the above composition as a buffering agent is inferior to the performance of the adjuvant compositions of the present invention. The compositions are added to distilled water having a pH of 10.

| Composition with phosphate ester | | Composition without phosphate ester | |
| --- | --- | --- | --- |
| % volume | pH | % volume | pH |
| 0 | 10 | 0 | 10 |
| 0.25 | 6.5 | 0.25 | 8.0 |
| 0.50 | 4.5 | 0.50 | 8.0 |
| 0.75 | 4.0 | 0.75 | 7.8 |
| 1.00 | 3.5 | 1.00 | 7.8 |
| 1.50 | 3.4 | 1.50 | 7.8 |
| 1.75 | 3.3 | 1.75 | 7.5 |
| 2.00 | 3.2 | 2.00 | 7.5 |

Without the phosphate ester, the composition does not reduce the pH to the desired range of 4–6, or to the acidic range, and there is a loss of produce homogeneity because the components tend to separate upon standing.

Comparative example B

The following composition (Composition B) provided a combination of paraffinic spray oil and phosphate ester without the sorbitan ester.

| Ingredient | % |
| --- | --- |
| Paraffin Oil (Sun Spray 11NTM) | 83.0 |
| 4 POE Nonyl phenol | 12.0 |
| 4 POE alkyl aryl phosphate | 2.0 |
| Stearic acid | 1.0 |
| Oleic acid | 2.0 |
| | 100.0 |

Although the buffer performance was acceptable, the emulsion performance was very poor in comparison with the compositions of the present invention. The composition without the sorbitan ester was not stable and the components separated out upon standing.

Emulsion performance for agricultural formulations is usually evaluated by means of World Health Organization (WHO) method number SIF/31.R2. Utilizing this procedure in the evaluation of examples A+B produces the following results for a 5% by volume mix in 342 ppm water:

EMULSION STABILITY PERFORMANCE (measured as amount of oil separated from the water/adjuvant mix in ml vs. time)

| SEPARATION OF COMPOSITION 1 | SEPARATION OF COMPOSITION A | SEPARATION OF COMPOSITION B | TIME IN MINUTES |
| --- | --- | --- | --- |
| 0 | 0 | 1.25 | 5 |
| 0 | 0 | 1.75 | 10 |

-continued

| SEPARATION OF COMPOSITION 1 | SEPARATION OF COMPOSITION A | SEPARATION OF COMPOSITION B | TIME IN MINUTES |
|---|---|---|---|
| 0 | trace | 2.25 | 15 |
| trace | trace | 2.25 | 20 |
| 0.5 | 0.25 | 2.25 | 25 |
| 1.0 | 1.0 | 2.25 | 30 |
| 1.0 | 1.0 | 2.25 | 45 |
| 1.0 | 1.0 | 2.25 | 60 |
| 1.0 | 1.0 | 2.25 | 120 |
| 1.5 | 1.0 | 2.25 | 24 |

The surfactant type and amount is selected based on emulsion stability performance. The tests are performed on the composition in combination with the buffering agent and spray oil. The guidelines below determine the degree of preference.

| Separation (Preferred) (ML) | Separation Most Preferred (ML) | Time in Minutes |
|---|---|---|
| 0 | 0 | 5 |
| trace | 0 | 15 |
| 1.00 | 0.5 | 30 |
| 1.50 | 1.00 | 45 |
| 1.75 | 1.00 | 60 |
| 2.00 | 1.00 | 120 |

| | | |
|---|---|---|
| (2) Spray Oil | 80.00 | |
| Nonyl Phenol Ethoxylate (6-mole) | 18.00 | |
| Acetic Acid | 2.00 | |
| | 100.00 | |
| (3) Spray Oil | 80.00 | |
| Nonyl Phenol Ethoxylate (5-6 mole) | 18.00 | |
| Propionic Acid | 2.00 | |
| | 100.00 | |
| (4) Spray Oil | 80.00 | |
| Nonyl Alcohol Ethoxylate (6 mole) | 18.00 | |
| Acetic Acid | 2.00 | |
| | 100.00 | |
| (5) Spray Oil | 83.00 | |
| Stearyl Alcohol Ethoxylate 4-5 mole | 15.00 | |
| Acetic Acid | 1.00 | |
| Lactic Acid | 1.00 | |
| | 100.00 | |
| (6) Spray Oil | 80.00 | |
| Nonyl phenol Ethoxylate (5-6 mole) | 10.00 | |
| Carboxylated alcohol ethoxylate (5 mole) | 8.00 | |
| Acetic Acid | 2.00 | |
| | 100.00 | |
| (7) Spray Oil | 80.00 | |
| Nonyl Phenol Ethoxylate (5-6 mole) | 10.00 | |
| Acetic Acid | 2.00 | |
| Carboxylated alcohol ethoxylate (5 mole) | 5.00 | |
| Silicone Surfactant (Silvet L-77) | 3.00 | |
| | 100.00 | |
| (8) Spray Oil | 80.00 | |
| Nonyl Phenol Ethoxylate | 10.00 | |
| PEG Ester Ethoxylate (6 moles) | 5.00 | |
| Acetic Acid | 1.00 | |
| Citric Acid | .50 | |
| Glutaric | .50 | |
| Carboxylated alcohol ethoxylate (5 mole) | 3.00 | |
| | 100.00 | |

I claim:

1. A homogeneous, essentially nonaqueous adjuvant composition consisting essentially of a spray oil having a minimum of 85% of unsulfonated residue value, a surfactant blend selected from the group consisting of
(a) fatty alkanolamides of the formula

wherein R is a $C_6$-$C_{25}$ alkyl group; R and R″ are the same or different and are independently selected from the group consisting of hydrogen, —$CH_2CH_2OH$ and $$-CH_2-\underset{\underset{CH_3}{|}}{CH}-OH$$

(b) PEG esters of the formula

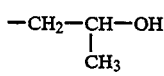

wherein $R^2$ is a $C_2$-$C_{25}$ fatty alkyl, $R^3$ is a $C_2$-$C_{25}$ fatty alkyl or hydrogen and m is a number from 1 to 100,
(c) silicone surfactants of the formula

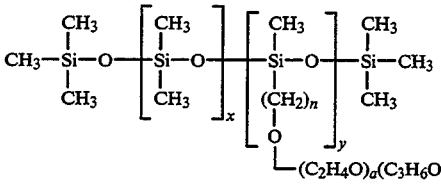

wherein x is a number from 0 to 5, y is a number from 1 to 5, a is a number from 3 to 25, b is a number from 0 to 25, n is a number from 2 to 4 and $R^6$ is hydrogen, an alkyl group having 1 to 4 carbon atoms or an alkyl ester group having 1 to 4 carbon atoms,
(d) ethoxylated fatty acids

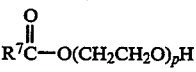

wherein $R^7$ is a $C_6$-$C_{25}$ alkyl group, p is a number from 1 to 100,
(e) alkyl ethoxylates

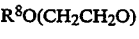

wherein $R^8$ is alkyl group and q is a number from 1 to 100,
(f) alkylphenol ethoxylates

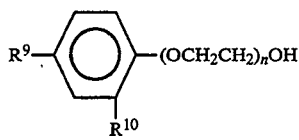

wherein $R^9$ is hydrogen or $C_1$-$C_{20}$ alkyl, $R^{10}$ is hydrogen or $C_1$-$C_{20}$ alkyl and n is a number from 1 to 100,
(g) polypropylene glycols

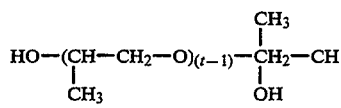

wherein t is a number from 1 to 100,
(h) amine ethoxylates

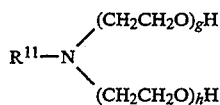

wherein g and h are numbers from 1 to 100 and R' is a $C_1$-$C_{25}$ alkyl and
(i) mixtures of any of the above surfactants (a) through (h), and a buffering agent is in an amount sufficient to reduce the pH to below 7.

2. A composition as claimed in claim 1 wherein the buffering agent is selected from the group consisting of alkylaryl polyethoxy phosphate ester, $C_1$-$C_6$ carboxylic acids, $C_1$-$C_6$ dicarboxylic acids, phosphoric acid, citric acid, glutaric acid, gluconic acid, lactic acid, glycolic acid, acrylic acid, and carboxylated alcohol ethoxylate.

3. A composition according to claim 2, wherein the spray oil comprises a paraffin oil having a distillation range of about 400° F. to about 450° F. at 10 mm Hg.

4. A composition according to claim 2, wherein the spray oil comprises a paraffin oil having a distillation range of about 460° F. to about 470° F. at 10 mm Hg.

5. A composition according to claim 2, comprising 80 to 85% by weight spray oil and about 5 to 20% by weight of the surfactant blend based on the total weight of the composition.

6. A composition as claimed in claim 5, wherein the buffering agent is 0.5 to 10% by weight based on the total weight of the composition.

7. A composition as claimed in claim 6, wherein the buffering agent is 0.5 to 5% by weight based on the total weight of the composition.

8. A composition according to claim 1, wherein the surfactant blend consists of nonyl phenol ethoxylate.

9. A composition according to claim 8, wherein the surfactant blend consists of nonyl phenol ethoxylate in an amount of about 18%.

10. A composition according to claim 8, wherein the buffering agent is acetic acid.

11. A composition according to claim 8, wherein the buffering agent is propionic acid.

12. A composition according to claim 1 wherein the surfactant blend consists of nonyl alcohol ethoxylate and the buffering agent is acetic acid.

13. A composition according to claim 1, wherein the surfactant blend consists of stearyl alcohol ethoxylate and the buffering agent is a mixture of acetic and lactic acid.

14. A composition according to claim 1, wherein the surfactant blend consists of nonyl phenol ethoxylate and the buffering agent is a mixture of carboxylated alcohol ethoxylate and acetic acid.

15. A composition according to claim 1, wherein the surfactant blend consists of the mixture of nonyl phenol ethoxylate and a silicone surfactant.

16. A composition according to claim 15, wherein the buffering agent is a mixture of acetic acid and carboxylated alcohol ethoxylate.

17. A composition according to claim 1, wherein the surfactant blend is a mixture of nonyl phenol ethoxylate and PEG ester ethoxylate.

18. A composition according to claim 17, wherein the buffering agent is a mixture of acetic acid, citric acid, glutaric and carboxylated alcohol ethoxylate.

19. A process to control insects comprising spraying the composition as claimed in claim 1.

20. A homogeneous, essentially nonaqueous adjuvant composition consisting essentially of a spray oil having a minimum of 85% of unsulfonated residue value, a surfactant blend selected from the group consisting of
(a) fatty alkanomides of the formula

wherein R is a $C_6$-$C_{25}$ alkyl group; R and R' are the same or different and are independently selected from the group consisting of hydrogen, —$CH_2CH_2OH$ [or-]and

—$CH_2CH$—OH
|
$CH_3$ (b) PEG esters of the formula

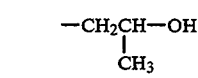

wherein $R^2$ is a $C_2$-$C_{25}$ fatty alkyl, $R^3$ is a $C_2$-$C_{25}$ fatty alkyl or hydrogen and m is a number from 1 to 100,
(c) silicone surfactants of the formula

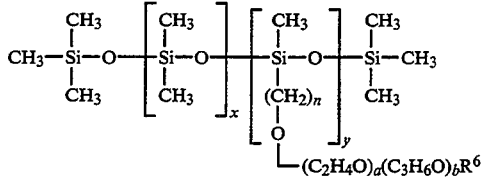

wherein x is a number from 0 to 5, y is a number from 1 to 5, a is a number from 3 to 25, b is a number from 0 to 25, n is a number from 2 to 4 and $R^6$ is a hydrogen, an alkyl group having 1 to 4 carbon atoms or an alkyl ester group having 1 to 4 carbon atoms,
(d) ethoxylated fatty acids

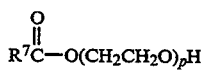

wherein $R^7$ is a $C_6$-$C_{25}$ alkyl group, p is a number from 1 to 100, (e) alkyl ethoxylates

wherein $R^8$ is alkyl group and q is a number from 1 to 100, (f) alkylphenol ethoxylates

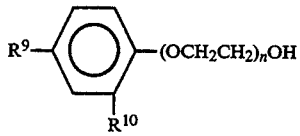

wherein $R^9$ is hydrogen or $C_1$-$C_{20}$ alkyl, $R^{10}$ is hydrogen or $C_1$-$C_{20}$ alkyl and n is a number from 1 to 100, (g) polypropylene glycols

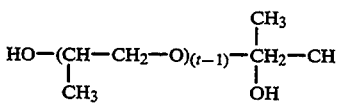

wherein t is a number from 1 to 100, (h) amine ethoxylates

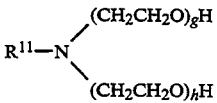

wherein g and h are numbers from 1 to 100 and $R_{11}$ is a $C_1$-$C_{25}$ alkyl and (i) mixtures of any of the above surfactants (a) through (h), and a buffering agent is in an amount sufficient to reduce the pH to below 7, wherein said surfactant blend is mixed with sorbitan fatty acid ester and/or a polyethoxylated derivative of a sorbitan fatty acid ester.

* * * * *